United States Patent [19]

Wright et al.

[11] Patent Number: 4,948,593
[45] Date of Patent: Aug. 14, 1990

[54] OSMOTIC DOSAGE FORM COMPRISING AN ESTROGEN AND A PROGESTOGEN

[75] Inventors: Jeri D. Wright, Dublin; Jerry D. Childers, Fremont; Brian L. Barcley, Sunnyvale; Patrick S. L. Wong, Palo Alto; Linda E. Atkinson, Portola Valley, all of Calif.

[73] Assignee: Alza Corporation, Palo Alto, Calif.

[21] Appl. No.: 351,365

[22] Filed: May 15, 1989

[51] Int. Cl.$^5$ .............................................. A61K 9/22
[52] U.S. Cl. ...................................... 424/473; 424/422
[58] Field of Search .............................. 424/422–426, 424/473

[56] References Cited

U.S. PATENT DOCUMENTS 4,344,431 8/1982 Yolles .................................. 424/425
4,449,983 5/1984 Cortese et al. ................... 424/424 X Primary Examiner—Thurman K. Page
Attorney, Agent, or Firm—Paul L. Sabatine; Edward L. Mandell; Steven F. Stone

[57] ABSTRACT

An osmotic device is disclosed comprising an estrogenic and a progestogenic steroid that are delivered as a contraceptive pair for fertility regulation in a female.

11 Claims, 5 Drawing Sheets

FIG_7
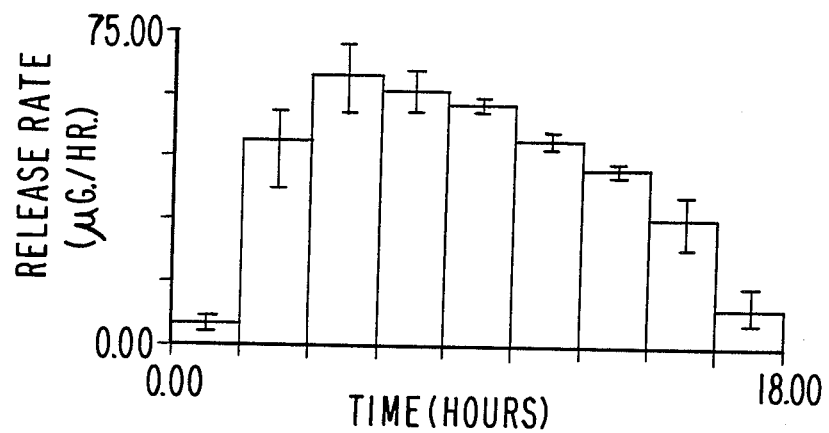
FIG.8
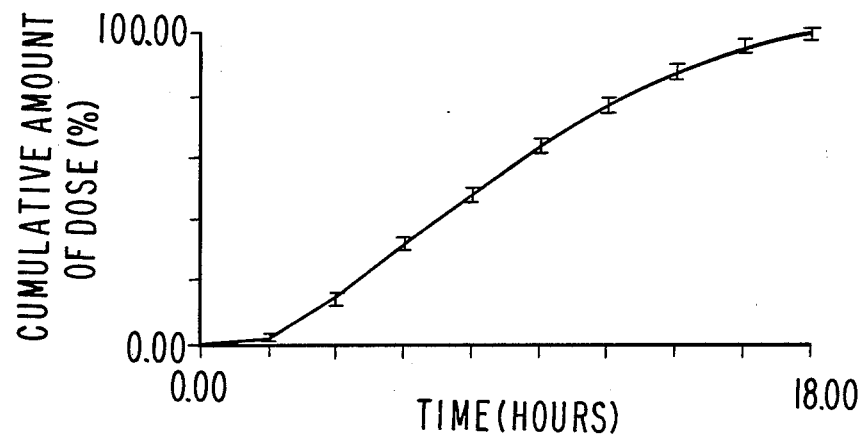

OSMOTIC DOSAGE FORM COMPRISING AN ESTROGEN AND A PROGESTOGEN

FIELD OF THE INVENTION

This invention pertains to an osmotic dosage form comprising an estrogen and a progestogen. The invention concerns also a method of orally administering the osmotic dosage form for delivering the estrogen and the progestogen for contraception.

BACKGROUND OF THE INVENTION

A pressing need exists for a dosage form for administering to human females for contraception an estrogen and a progestogen at a rate controlled by the dosage form. The need existed since early 1960 when oral contraceptive pills comprising an estrogen and a progestogen became available for contraception. The contraceptive pills used by the prior art delivered the estrogenic and the progestational steroids in tablet form, that is, in a bulk, nonrate controlled amount. The contraceptive steroids were delivered heretofore unprotected from the changing environment of the gastrointestinal tract and with little consideration for the pharmacological and the physiological needs of the recipient. The contraceptive steroids were delivered by the prior art as an oral pill devoid of rate controlled delivery because contraceptive steroids are practically insoluble in aqueous media. Thus, the steroids do not lend themselves for manufacture into a dosage form that administers the steroids at a controlled and known rate per unit time.

In light of the above presentation it will be appreciated by those having skill in the dispensing art to which this invention pertains that a pressing need exists for a dosage form that can deliver to a recipient at a controlled rate in a known amount per unit time the valuable estrogen and progestogen for contraception. The pressing need exists for an oral dosage form that can deliver estrogen and progestogen simultaneously at controlled rate in substantially constant doses per unit time over a prolonged period of time for their contraceptive effects, and substantially independent of the variable environment of the gastrointestinal tract. It will be further appreciated by those skilled in the contraceptive art that such a novel and unique dosage form that can administer the two contraceptive steroids in rate-controlled doses over time and, simultaneously, provide contraception would represent an advancement and a valuable contribution to the art.

OBJECT OF THE INVENTION

Accordingly, in view of the above presentation, it is an immediate object of this invention to provide a dosage form for delivering estrogen and progestogen in rate controlled amounts, and which dosage form substantially overcomes the deficiencies and omissions associated with the prior art.

Another object of the present invention is to provide an osmotic dosage form for co-administering an estrogen and a progestogen in rate controlled doses over a prolonged period of time for contraception in a warm-blooded female.

Another object of the invention is to provide a pharmaceutically acceptable osmotic dosage form that makes available sustained and controlled estrogen and progestogen contraceptive activity.

Another object of the invention is to provide a novel dosage form manufactured as an osmotic device that can administer the steroidal estrogen and progestogen to a biological receptor site to produce the desired contraceptive effect, and which osmotic dosage form substantially reduces and/or substantially eliminates the unwanted influences of the gastrointestinal environment on the steroids while they reside in the dosage form, and still provides controlled administration of both the estrogen and progestogen over time.

Another object of the present invention is to provide an osmotic dosage form that can deliver the substantially insoluble estrogen and progestogen at a controlled and known contraceptive rate over time.

Another object of the present invention is to provide an osmotic dosage form adapted for oral administration of an estrogen and a progestogen, which dosage form comprises a first composition comprising the estrogen and the progestogen, and a contacting second composition that operate together for the controlled administration of both the estrogen and the progestogen over time.

Another object of the present invention is to provide a complete contraceptive regimen comprising an osmotic dosage form and a method of contraception, the use of which osmotic dosage form and method of contraception requires intervention only for initiation of the contraceptive regimen.

Another object of the invention is to provide a composition of matter comprising an estrogen, a progestogen and an osmopolymer, which composition can be stored in and dispensed by an osmotic device for the purpose of fertility control.

Another object of the invention is to provide a laminated article of manufacture, which laminate comprises a first lamina comprising an estrogen, a progestogen and an osmopolymer, and a second lamina comprising a different osmopolymer, which laminate is useful for manufacturing an osmotic dosage form for fertility control.

Another object of the invention is to provide a method for producing contraception by orally administering an estrogen and a progestogen in a rate controlled dosage per unit time to a warm-blooded animal desiring fertility control.

Other objects, features, and advantages of the invention will be apparent to those skilled in the dispensing arts from the following detailed specification, taken in conjunction with the drawing figures and the accompanying claims.

BRIEF DESCRIPTION OF THE DRAWINGS

In the drawing figures, which are not drawn to scale but are set forth to illustrate various embodiments of the invention, the figures are as follows:

FIG. 3 is an opened view of the osmotic dosage form of FIG. 1 and FIG. 2, wherein FIG. 3 depicts the wall of the osmotic dosage form bearing an exterior fluid-soluble lamina comprising an estrogen, or a progestogen, or an estrogen and a progestogen;

FIGS. 5 through 12 depict rate of release and cumulative amounts of contraceptive steroids released by the dosage form of this invention.

In the drawings and in the specification like parts in related figures are identified by like numbers. The terms appearing earlier in the specification and in the description of the drawings, as well as embodiments thereof, are further described elsewhere in the disclosure.

DETAILED DESCRIPTION OF THE DRAWING FIGURES

Figure 1:
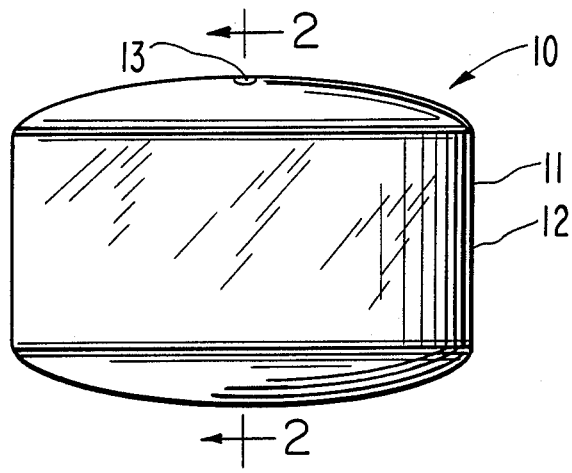
FIG. 1 is a view of an osmotic dosage form adapted and shaped for orally administering an estrogen and a progestogen to the gastrointestinal tract of a warm-blooded female.

Turning now to the drawing figures in detail, which drawing figures are preferred examples of the dosage forms provided by this invention and which examples are not to be construed as limiting, one example of the dosage form is illustrated in FIG. 1 and designated by the numeral 10. In FIG. 1, dosage form 10 comprises a body member 11, which body member 11 comprises a wall 12 that surrounds and encloses an internal compartment, not seen in FIG. 1. Dosage form 10 comprises at least one exit means 13 that connects the interior of dosage form 10 with the exterior biological environment of use.

Figure 2:
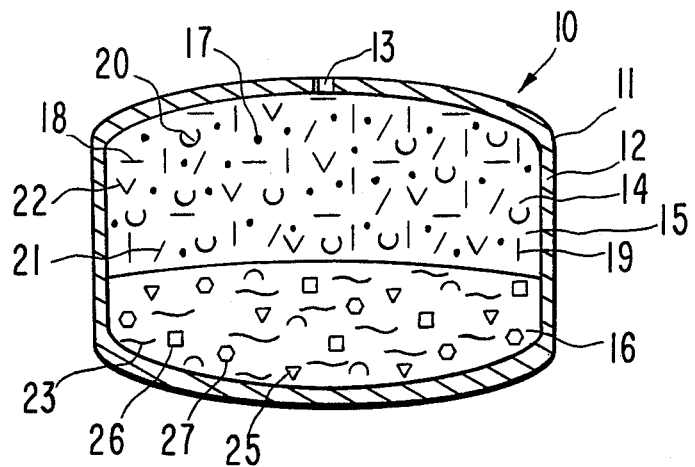
FIG. 2 is an opened view of the dosage form of FIG. 1, through 2—2, for illustrating the internal structure of the dosage form comprising the estrogen and the progestogen.

In the drawing FIG. 2, dosage form 10 is seen in opened view through 2—2 of FIG. 1. In FIG. 2, dosage form 10 is manufactured as an osmotic device. The osmotic dosage form 10 comprises a body 11, a wall 12, which wall 12 surrounds and defines an internal compartment 14. Wall 12 comprises at least one exit means 13 that connects internal compartment 14 with the exterior of dosage form 10. Dosage form 10 can comprise more than one exit means 13. Wall 12 of dosage form 10 comprises in at least a part a semipermeable composition that is permeable to the passage of an exterior fluid present in the environment of use, and wall 12 is substantially impermeable to the passage of contraceptive steroids and other ingredients present in compartment 14. The composition comprising wall 12 is substantially inert, and it maintains its physical and chemical integrity during the dispensing life of contraceptive steroids from osmotic dosage form 10. The phrase, "keeps its physical and chemical integrity," means wall 12 does not lose its structure and it does not change chemically during the contraceptive steroid dispensing life of dosage form 10.

Wall 12 comprises a cellulosic polymer composition. The cellulosic polymer comprises a member selected from the group consisting of a cellulose ester, cellulose ether, cellulose ester-ether, cellulose acylate, cellulose diacylate, cellulose triacylate, cellulose acetate, cellulose diacetate, and cellulose triacetate. The cellulosic polymers can comprise a degree of substitution, D.S., on the anhydroglucose unit from greater than 0 up to 3, inclusive. By degree of substitution is meant the average number of hydroxyl groups originally present on the anhydroglucose unit comprising the cellulose polymer that are replaced by a substituting group. Exemplary polymers comprise cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a D.S. of 2 to 3 and an acetyl content of 35 to 44.8%, and the like. Other examples comprise cellulose propionate having a D.S. of 1.8, a propanol content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentale, and the like. Additional cellulosic polymers comprise ethyl cellulose comprising an ethoxy group degree of substitution of 1.5 to 3, about 40% to 50% ethoxy content, and the like. In one preferred manufacture wall 12 comprises 100 weight percent (wt %) of a cellulosic polymer disclosed above. In another manufacture wall 12 can comprise from 70 weight percent to 100 weight percent of a cellulose polymer as disclosed above; from 0 weight percent to 30 weight percent of a member selected from the group consisting of a cellulose ether selected from the group consisting of hydroxypropylcellulose, hydroxyypropylmethylcellulose and hydroxyethylcellulose; and from 0 weight percent to 30 weight percent of polyethylene glycol; with the total amount of all components comprising wall 12 equal to 100 weight percent. The cellulosic polymers are known in U.S. Pat. Nos. 3,133,132; 3,845,770; 3,916,899 and 4,160,000; and in the *Handbook of Common Polymers* by Scott, J. R. and Roff W. J., (1971) published by CRC Press Cleveland, Ohio.

Internal compartment 14 comprises a first layer 15 and a second layer 16. The first layer 15 can be defined optionally as a first composition 15, and the second layer 16 also can be defined optionally as second composition 16. The first layer 15 and the second layer 16 initially are in laminar arrangement and they cooperate with each other and with osmotic dosage form 10 for delivering contraceptively effective amounts of contraceptive estrogen and progestogen steroids from dosage form 10.

The contraceptive steroids possessing estrogenic activity present in first layer 15 that can be dispensed by dosage form 10 to a warm-blooded female recipient comprise estrogen steroids 17 represented by dots. The estrogenic active steroids comprise a member selected from the group consisting of estradiol, estradiol valerate, estradiol benzoate, estradiol cypionate, estradiol propionate, estradiol dipropionate, estradiol acetate, ethinyl estradiol, 17α-ethinyl estradiol esters, 17α-ethinyl estradiol acetate, 17α-ethinyl estradiol benzoate, 17α-ethinyl estradiol ethers, estrone, estrone acetate, estrone sulfate, estriol, estriol succinate and estriol triacetate.

The contraceptive steroids possessing progestogenic activity present in first layer 15 that can be dispensed by dosage form 10 to a warm-blooded female recipient comprise the progestogen steroids represented by horizontal dashes 18. The progestogens comprise a member selected from the group consisting of progesterone, norethindrone, levonorgestrel sometimes known as d-norgestrel, norgestimate, 3-keto-desogestrel, desogestrel, gestodene, norethisterone, norethisterone acetate, norethynodrel, norethindrone acetate, 17-hydroxyprogesterone, 17-hydroxyprogesterone esters, 19-nor-17-hydroxyprogesterone, 19-nor-17-hydroxyprogesterone esters, 17α-ethinyl-testosterone, 17α-ethinyl-19-nortestosterone, D-17β-acetoxy-13β-ethyl-17α-ethinyl-gon-4- en-3-one oxime, d-13β-ethyl-17α-ethinyl-17β-hydroxygon-4-en-3-one, 13β-ethyl-17β-hydroxygon-4-en-3-one, 13β,17α-diethyl-17β-hydroxygon-4-en-3 one, ethylnodiol diacetate, medroxyprogesterone, medroxyprogesterone acetate, megestrol acetate, chlormadione acetate, dimethistrone, and 17α-ethinyl-17β-acetoxy-19-norandrost-4-en-3-one oxime.

Dosage form 10 effects fertility control by orally administering low contraceptively effective doses of a combination of an estrogen and a progestogen. The invention provides a multiplicity of dosage form 10 comprising an estrogen and a progestogen in various doses. The invention provides (a) dosage form wherein the estrogen concentration is the same in a number of dosage forms and the progestogen concentration changes in these dosage forms, and (b) dosage form wherein the estrogen concentration changes in the dosage form and the progestogen concentration is the same in the dosage form. Generically, the invention provides an osmotic dosage form comprising 0.002 mg to 1.000 mg of an estrogenically active steroid, and from 0.005 mg to 250 mg of a progesteronically active steroid.

More specifically, the first layer 15 comprises 0.035 mg of ethinyl estradiol and 0.40 mg of norethindrone, 0.035 mg of ethinyl estradiol and 0.50 mg of norethindrone, 0.035 mg of ethinyl estradiol and 0.75 mg of norethindrone, 0.035 mg of ethinyl estradiol and 1.0 mg of norethindrone, 0.035 mg of ethinyl estradiol and 0.25 mg of d-norgestrel, 0.020 mg of ethinyl estradiol and 0.25 mg of d,l-norgestrel, 0.020 mg of ethinyl estradiol and 0.75 mg of d,l-norgestrel, 0.035 mg of ethinyl estradiol and 0.50 mg of d,l-norgestrel, 0.035 mg of ethinyl estradiol and 0.75 mg of d,l-norgestrel, 0.050 mg of ethinyl estradiol and 0.125 mg of d,l-norgestrel, 0.040 mg of ethinyl estradiol and 0.250 mg of d,l-norgestrel, 0.030 mg of ethinyl estradiol and 0.50 mg of norethisterone, 0.035 mg of ethinyl estradiol and 0.80 mg of norethisterone, 0.035 mg of ethinyl estradiol and 1.0 mg of norethisterone, 0.030 mg of ethinyl estradiol and 0.05 mg of levonorgestrel, 0.040 mg of ethinyl estradiol and 0.075 mg of levonorgestrel, 0.030 mg of ethinyl estradiol and 0.125 mg of levonorgestrel, 0.035 mg of ethinyl estradiol and 0.180 mg of norgestimate, 0.035 mg of ethinyl estradiol and 0.200 mg of norgestimate, 0.050 mg of estradiol valerate and 0.75 mg of levonorgestrel, 0.060 mg of estrone acetate and 0.80 mg of norethindrone, 0.040 mg of estradiol propionate and 0.75 mg of 17α-ethinyl-19-nortestosterone, 0.050 mg of estriol and 0.80 mg of D-17β-acetoxy-13β-ethyl-17α-ethinyl-17βhydroxygon-4-en-3-one oxime, 0.040 mg estriol and 0.75 mg of D-13βethyl-17α-ethinyl-17β-hydroxygon-4-en-3-one, and the like.

This invention provides unexpectedly an osmotic delivery system 10 that comprises both an estrogenic steroid 17 and a progestogenic steroid 18 in a deliverable composition 15 for their concomitant delivery by the osmotic system for contraception. It is unexpected and unforeseen that an estrogenic steroid and a different progestogenic steroid can be housed together and delivered simultaneously at a rate controlled by the dosage system in a dose amount that corresponds to their dosage in the osmotic system. This is so as the estrogenic and the progestogenic steroid each possess different dispensing kinetics, different composition forming properties, different physical properties, different structures, different biological and therapeutic activities, different solubilities, and different concentrations in the dosage forms. The estrogenic and the progestogenic steroid are in the osmotic system substantially-free of interaction, and they are available in the dosage form for dispensing for immediate and future use to be simultaneously administered in a contraceptively effective dose.

First layer 15 comprises additionally from 20 mg to 300 mg of a polyethylene oxide possessing a molecular weight of about 50,000 to 350,000 as identified by vertical dashes 19, from 0 mg to 50 mg of a hydroxypropylmethylcellulose possessing a molecular weight of 9,200 to 22,000 as identified by saucers 20, from 0 mg to 20 mg of a polyvinyl pyrrolidone possessing a molecular weight of about 8,000 to 55,000 and identified by slanted dashes 21, and from 0 mg to 7.5 mg of a lubricant such as magnesium stearate or stearic acid, and the like, and identified the letter v with the accompanying number 22.

Second layer 16 comprises additionally, in a presently preferred manufacture, comprises from 20 mg to 300 mg of a polyethylene oxide exhibiting a molecular weight of about 2,000,000 to 7,500,000 as identified by wavy lines 23, from 0 to 50 mg of an acrylic carboxyl polymer possessing a molecular weight of 1,250,000 to 4,000,000 and identified by inverted half-circles 24, from 0 mg to 40 mg of an osmagent selected from the group consisting of sodium chloride, potassium chloride, and the like, and identified by triangle 25, from 0 mg to 30 mg of a hydroxypropylmethylcellulose exhibiting a molecular weight of 9,200 to 20,000, identified by square 26, and from 0 mg to 5 mg of a lubricant such as magnesium stearate identified by hexagonal 27. Second layer 16 optionally comprises from 0.10 mg to 5 mg of ferric oxide, or optionally FD & C blue lake #1.

Figure 3:
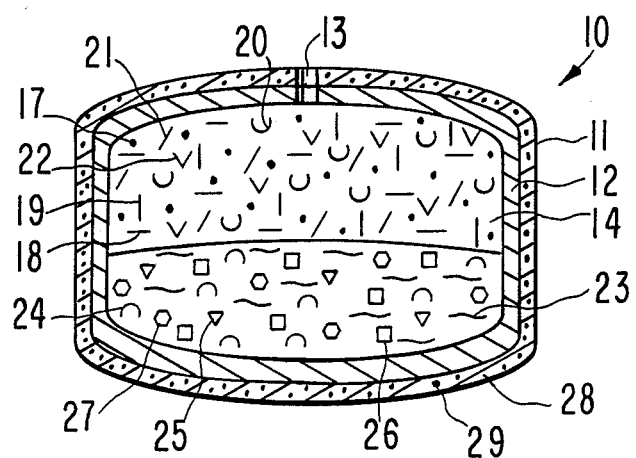

In FIG. 3, osmotic dosage form 10 is seen comprising an exterior lamina 28. Lamina 28 is coated onto the exterior surface of semipermeable wall 12. Lamina 28 comprises a composition represented by dots 29, which composition 28 comprises an estrogenic steroid, or a progestogenic steroid, or both an estrogenic and a progestogenic steroid. The composition comprises a hydroxypropylmethylcellulose carrier and, optionally, polyethylene glycol or, optionally, polyvinyl pyrrolidone, for making available instantly the contraceptive steroid, or contraceptive steroids, to a female receptor. Lamina coat 28 in operation dissolves or undergoes dissolution and delivers concurrently composition 29. Lamina 28 containing the contraceptive steroids, by providing immediate contraceptive steroid delivery, essentially overcomes the time required for the contraceptive steroids to be delivered from lumen 14 of device 10. A start-up time is needed for imbibing an exterior fluid through wall 12 causing second layer 16 to displace first layer 15 through exit passageway 13 to the biological environment of use. Lamina 28, in one presently preferred embodiment, comprises from 0.010 mg to 0.150 mg of an estrogenic steroid, or from 0.010 mg to 75.00 mg of progestogenic steroid, and from 0.50 mg to 100 mg of a hydroxypropylmethylcellulose possessing a molecular weight of 9,200 to 22,000, from 0 to 100 mg of polyethylene glycol and from 0 to 100 mg of polyvinylpyrrolidone. Lamina 28, in operation in fluid environment of use, begins to release the contraceptive steroid instantly, and it completely releases all the contraceptive steroid in lamina 28 during the first hour. This instant release thereby provides contraceptive steroid for immediate passage into the plasma of a recipient.

Figure 4:
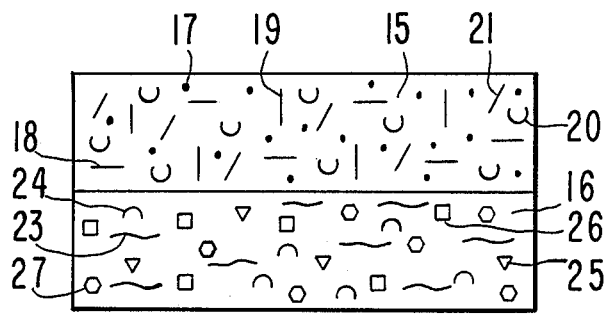
FIG. 4 illustrates a laminate comprising a first lamina comprising an estrogen, a progestogen and an osmopolymer, and a second lamina comprising an osmopolymer that is a different osmopolymer than the osmopolymer present in the first lamina.

Drawing FIG. 4 illustrates a laminate provided by the invention. The laminate comprises a first lamina 15 and a second lamina 16. The first lamina 15 comprises an estrogenic steroid 17, a progestational steroid 18, a polyethylene oxide 19 and an optional hydroxypropylmethylcellulose 20. The second lamina 16 comprises a polyethylene oxide 23 that is a different polyethylene oxide than the polyethylene oxide present in the first lamina 15. The second lamina 16, in another presently preferred manufacture, comprises additionally an acrylic carboxyl polymer 24, a osmagent 25, a hydroxypropylmethylcellulose 26 and a lubricant 27.

The expression, "exit means 13," as used herein, comprises means and methods suitable for the controlled metered release of estrogenic steroid 17 and progestogenic steroid 18 from compartment 14 of dosage form 10. Exit means 13 is sized and adapted for the simultaneous metered release of estrogenic steroid 17 and progestogenic steroid 18 from dosage form 10. Exit means 13 includes at least one passageway, orifice, or the like, through wall 12 for communicating with the contraceptive steroids in dosage form 10. The expression, "at least one passageway," includes aperture, orifice, bore, pore, porous element, and the like, through which the contraceptive steroids can migrate, a hollow fiber, capillary tube, porous overlay, porous insert, composite semipermeable contacting microporous insert, or the like. The expression includes also a material that erodes or is leached from wall 12 in a fluid environment of use to produce at least one passageway in wall 12. Representative materials suitable for forming at least one passageway, or a multiplicity of passageway, include an erodible polyglycolic acid, or a polylactic acid member in wall 12, a gelatinous filament, polyvinyl, alcohol, a leachable material such as a fluid removable pore forming polysaccharide, polyol, salts, oxide, or the like. A passageway, or a plurality of passageways can be formed by leaching a material such as sorbitol, fructose, maltose, lactose, or the like, from wall 12. The passageway 13 can have any shape such as round, triangular, square, elliptical, and the like, for assisting in the metered release of the contraceptive steroids from dosage form 10. Dosage form 10 can be constructed with one or more passageway in spaced apart relation, or more than one passageway on a single surface of dosage form 10 Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

Dosage form 10 of the present invention is manufactured by standard techniques. For example, in one embodiment the beneficial contraceptive steroids are mixed with the pharmaceutically acceptable osmopolymer that acts as a carrier for the contraceptive steroids, and with other presently preferred dosage forming ingredients and then pressed into a solid lamina possessing dimensions that correspond to the internal dimensions of the compartment space adjacent to the passageway. In another manufacture, the beneficial contraceptive steroids and other composition forming ingredients and a nontoxic solvent are mixed into a solid or a semisolid state, by conventional methods such as ballmilling, calendering, stirring or rollmilling, and then pressed into a preselected lamina-forming shape. Next, a lamina of a composition comprising an osmopolymer and an optional osmagent are placed in contact with the lamina comprising the beneficial contraceptive steroids, and the two lamina comprising the laminate are surrounded with a semipermeable wall. The lamination of the first beneficial fertility controlling steroid composition and the second osmopolymer composition can be accomplished by using a two-layer tablet press. The wall can be applied by molding, spraying or dipping the pressed shapes into wall forming compositions. Another preferred techniques that can be used for applying the wall is the air suspension coating procedure. This procedure comprises suspending and tubing the two layered laminates in a current of air until the wall forming composition surrounds the laminate. The exterior instant release coat comprising the contraceptive steroid can be formed also by using the air suspension technique. The air suspension procedure is well suited for independently forming a wall or an exterior lamina coat. The air suspension procedure is described in U.S. Pat. No. 2,799,241; in *J. Am. Pharm. Assoc.*, Vol. 48, pp 451–59, (1959); and ibid, Vol. 49, pp 82–84, (1960). Dosage forming systems also can be coated with the wall forming composition with a Wurster ® Air Suspension Coater, or an Aeromatic ® Air Suspension Coater can be used for applying the wall or the lamina. Other wall and lamina coating techniques such as pan coating can be used for manufacturing the dosage form. In the pan coating system wall forming or lamina forming compositions are deposited by successive spraying of the compositions on the contraceptive steroids accompanied by tumbling in a rotating pan. A pan coater is used to produce a thicker wall or lamina coat. A larger volume of methanol can be used in a cosolvent system to produce a thinner wall or a lamina. Finally, the wall or the lamina coated contraceptive steroids are dried in a forced air oven to free the dosage form of the solvents. Generally, the wall formed by these techniques will have a preferred thickness of 1 to 25 mils (0.03 to 0.64 mm) with a presently preferred thickness of 3 to 10 mils (0.08 to 0.26 mm), and the exterior lamina coat generally will have a thickness of 0.3 to 8 mils (0.008 to 0.20 mm). Of course, thicker walls are encompassed by the invention. Other manufacturing procedures are described in *Modern Plastic Encyclopedia*, Vol. 46, pp 62–70, (1969); and in *Pharmaceutical Sciences*, by Remington, 14th Ed., pp 1626–1978, (1970), published by Mack Publishing Co., Easton, PA.

The osmotically effective compounds, which are known also as osmagents, as osmotically effective solutes, and as osmotic enhancers, useful for the purpose of this invention, comprise a member selected from the group consisting of water soluble inorganic osmagents and water soluble organic osmagents. The osmagents include a member selected from the group consisting of magnesium sulfate, magnesium chloride, sodium chloride, potassium chloride, lithium sulfate, lithium chloride, potassium sulfate, choline chloride, and the like. The osmotically effective compounds are known in U.S. Pat. Nos. 4,177,256 and 4,449,983.

Exemplary solvents suitable for manufacturing the wall include inert inorganic and organic solvents that do not adversely harm the materials and the final wall. The solvents broadly include a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, water, acetone and water, acetone and methanol, acetone and ethyl alcohol, methylene dichloride and methanol, ethylene dichloride and methanol, and the like.

DETAILED DESCRIPTION OF EXAMPLES

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic dosage form adapted, designed and shaped for delivering contraceptive steroids is manufactured as follows: first, a contraceptive composition is prepared by passing through a 40 mesh screen 464.52 g of polyethylene oxide having a molecular weight of about 100,000. Then 7.33 g of norethindrone and 25 g of hydroxypropylmethylcellulose, having a number average molecular weight of 11,200, is added to the polyethylene oxide and the three ingredients mixed for about 10 minutes in a conventional mixer. While the three ingredients are mixing, a freshly prepared solution of 0.640 g of ethinyl estradiol dissolved in 375 ml of denatured, anhydrous ethanol is slowly added to the mixer and the mixing continued for an additional 10 minutes. The wet granulation is passed through a 20 mesh screen, dried at room temperature for 16 hours and passed again through a 20 mesh screen. Finally, 2.5 g of magnesium stearate is added to the granulation and all the ingredients mixed in a rollermill for 1 to 3 minutes.

The second composition is prepared by mixing 370.0 g of polyethylene oxide having a molecular weight of 4,000,000 with 100 g of sodium chloride and the homogeneous blend passed through a 40 mesh screen. Then, the just prepared mixture is mixed with 25.0 g of hydroxypropylmethylcellulose, having a number average molecular weight of 11,200, and with 2.5 g of nontoxic FD & C blue lake #1, for 10 minutes in a mixer. Then, 350 ml of denatured, anhydrous ethanol is added slowly to the blending mixture and all the ingredients mixed for an additional 5 minutes. The freshly prepared wet granulation is passed through a 20 mesh screen, allowed to dry at room temperature for 16 hours, and again passed through a 20 mesh screen. The screened granulation is mixed with 2.5 g of magnesium stearate in a rollermill for 1 minute.

A three-layered press is used for forming the laminate. First, 30 mg of the first composition comprising the contraceptive steroids is added to the press and tamped, then 30 mg of the second lamina forming composition is added to the press and the two laminae pressed into a contacting laminated arrangement.

Next, the laminate is surrounded with a semipermeable wall. The wall forming composition comprises 95% cellulose acetate, having an acetyl content of 39.8%, and 5% polyethylene glycol having a molecular weight of 3350. The wall forming composition is dissolved in acetone:water (90:10 wt:wt) solvent to make a 4% solids solution. The wall forming composition is sprayed onto and around this bi-laminate in an Aeromatic ® Air Suspension Coater.

The wall coated bi-laminates are dried for 24 hours at room temperature. Then, a 20 mil (0.5 mm) exit orifice is laser drilled on the contraceptive laminate side of the osmotic device. The residual solvent is removed by drying the osmotic system for 48 hours at 50° C. and 50% relative humidity. The osmotic systems are then dried for one hour at 50° C. to remove the excess moisture.

The osmotic system is given a color overcoat to enhance its aesthetic appearance. In one manufacture the osmotic systems are coated with a composition comprising 38.4 g of hydroxypropylmethylcellulose and 4.27 g of polyethylene glycol 3350 to produce a clear overcoat. In another manufacture the osmotic systems are coated with a composition comprising 21.87 g (10% by wt) of hydroxypropylmethylcellulose having a 11,200 molecular weight, 2.46 g (10% by wt) of polyethylene glycol having a 3350 molecular weight and 0.25 g (1.0% by wt) of FD & C blue lake #1 dye to produce a blue overcoat. In an optional manufacture the color overcoat can comprise hydroxypropylmethylcellulose and diethyl phthalate mixed with denatured alcohol: water (90:10 volume:volume) to make a 5% solution. The color composition is sprayed onto and around the drilled delivery system in an Aeromatic ® Air Suspension Coater. The residual solvent is removed by drying for 16 hours at 25° C. to yield the operative osmotic dosage form.

EXAMPLE 2

Figure 5:
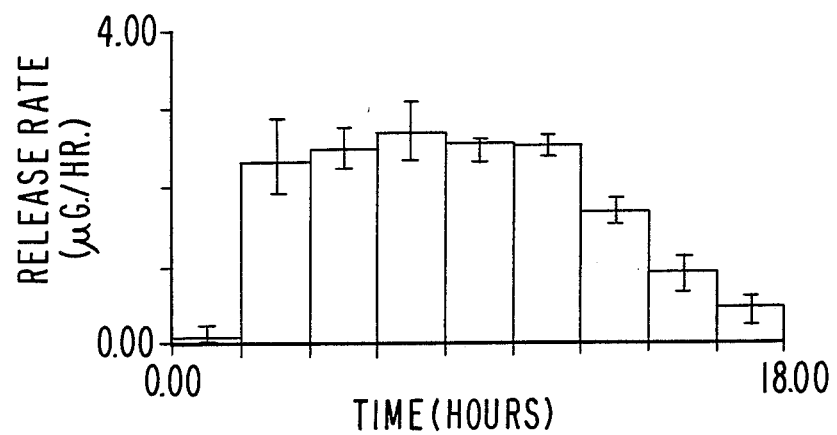
Figure 6:
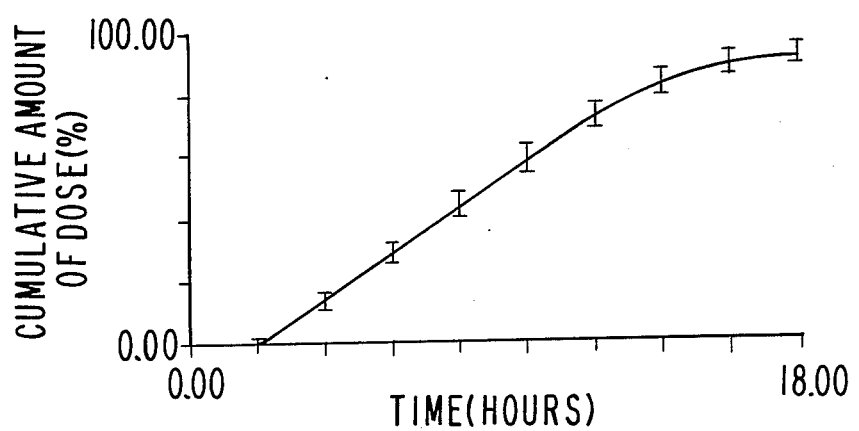

Following the procedure of Example 1, an osmotic dosage form is prepared comprising a first composition comprising 0.039 mg of ethinyl estradiol, 0.825 mg of norethindrone, 27.49 mg of polyethylene oxide having a 100,000 molecular weight, 1.5 mg of hydroxypropylmethylcellulose having a 11,200 molecular weight, and 0.15 mg of magnesium stearate; a second composition comprising 22.2 mg of polyethylene oxide having a 5,000,000 molecular weight, 6 mg of sodium chloride, 1.5 mg of a hydroxypropylmethylcellulose having a 11,200 molecular weight, 0.15 mg of blue dye and 0.15 mg of magnesium stearate; a wall comprising 6.65 mg of cellulose acetate, having a 43.5% acetyl content, and 0.35 mg of polyethylene glycol; a orifice diameter of 2.0 mils (0.52 mm), and an ethinyl estradiol rate of release of 2.158 μg/hr, and a norethindrone rate of release of 56.661 μg/hr. The rate of release per unit time over time for the ethinyl estradiol is seen in FIG. 5; the cumulative amount of ethinyl estradiol released over a prolonged period of time is seen in FIG. 6; the rate of release of norethindrone per unit time is depicted in FIG. 7, and the cumulative amount of norethindrone released over time is seen in FIG. 8.

EXAMPLE 4

Figure 9:
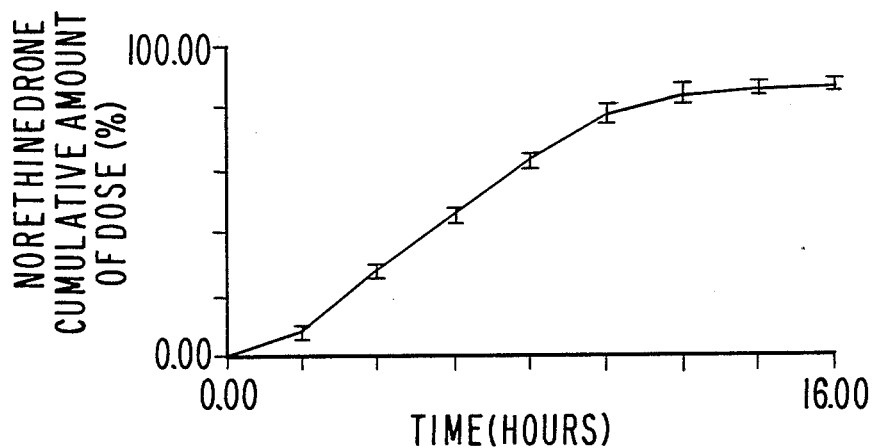
Figure 10:
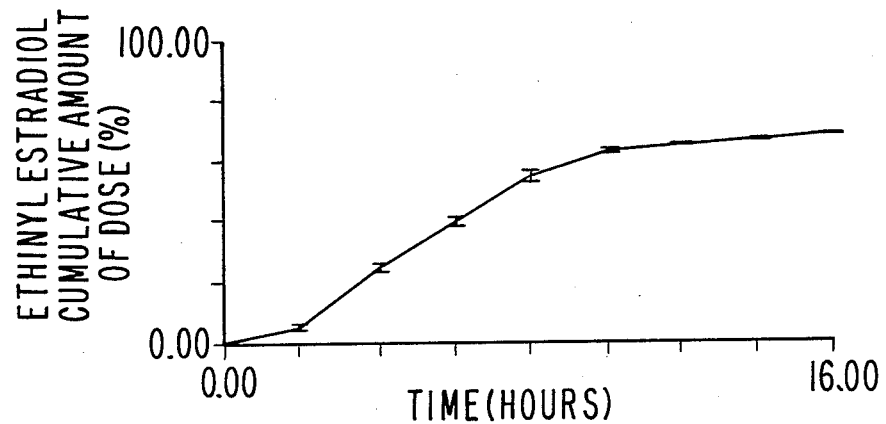

The procedure of Example 1 is followed in this example to prepare an osmotic dosage form comprising a first, displaceable composition comprising 0.801 mg of norethindrone, 0.036 mg of ethinyl estradiol, 27.513 mg of polyethylene oxide having a 200,000 molecular weight, 1.5 mg of polyvinyl pyrrolidone, and 0.15 mg of magnesium stearate; a second composition comprising 22.05 mg of polyethylene oxide having a 4,000,000 molecular weight, 6.0 mg of sodium chloride, 1.5 mg of hydroxypropylmethylcellulose having a 11,200 molecular weight, 0.30 mg of pharmaceutically acceptable blue dye, and 0.15 mg of magnesium stearate; a wall comprising 5.70 mg of cellulose acetate having a 43.5% acetyl content, and 0.30 mg of polyethylene oxide; an orifice having a diameter of 20 mils (0.25 mm), a cumulative release rate for norethindrone as seen in FIG. 9, and a cumulative release rate for ethinyl estradiol as seen in FIG. 10. The dosage form released 75.179 μl/hr of norethindrone and 2.883 μg/hr of ethinyl estradiol.

EXAMPLE 5

An osmotic dosage form comprising means for immediately administering an estrogenic steroid from an external composition followed by prolonged administration of an estrogenic and progestogenic contraceptive pair is prepared according to Example 1. In this example, a steroid overcoat composition comprising 0.324 g of ethinyl estradiol and 42.67 g of Opadry ® carrier, a hydroxypropylcellulose carrier, are dissolved in denatured alcohol:water (90:20 v:v) and sprayed onto the outer surface of the wall of the osmotic system. Then, a seal coat composition comprising hydroxypropylmethylcellulose and polyethylene glycol (9:1 wt:wt), dissolved in denatured alcohol (90:10 v:v) solvent to make a 5% solids solution is sprayed onto the ethinyl estradiol osmotic systems. The osmotic systems are dried for 16 hours at 35° C. to remove the residual solvent. The final concentration of the ethinyl estradiol in the exterior composition is 0.007 mg.

EXAMPLE 6

An osmotic dosage form comprising means for the immediate administration of a progestogenic steroid from an external composition, followed by the twenty-four administration of an estrogenic and progestogenic contraceptive pair, is prepared according to Example 1. In this example a steroid overcoat comprising 3.703 g of norethindrone and 38.4 g of hydroxypropylmethylcellulose and 4.27 g of polyethylene glycol are dissolved in denatured, anhydrous ethanol and distilled water (11:2 v:v) and sprayed onto the exterior surface of the semipermeable wall, in an Aeromatic ® Air Suspension Coater. Immediately following a sealer coat comprising 21.87 g of hydroxypropylmethylcellulose, 2.46 g of polyethylene glycol and 0.25 g of FD & C blue lake #1 dissolved in denatured anhydrous alcohol and distilled water (90:10 v:v) solvent, to make a 5% solids solution, is sprayed onto the norethindrone overcoat. The osmotic systems are dried for 16 hours at 35° C. to remove residual solvent. The final concentration of the norethindrone in the exterior composition is 0.400 mg.

EXAMPLE 7

Following the procedure in Example 1, an osmotic device is manufactured comprising a first composition comprising ethinyl estradiol and norgestrel for delivering 0.035 mg of the ethinyl estradiol and 0.50 mg of the d,l-norgestrel; 84.75 weight percent polyethylene oxide having a 200,000 molecular weight, 10 weight percent hydroxypropylmethylcellulose, having a number average molecular weight of 11,200, and 0.25 weight percent magnesium stearate; a second composition comprising 64.75 weight percent polyethylene oxide, having a 7,500,000 molecular weight, 24 weight percent sodium chloride, 10 weight percent hydroxypropylmethylcellulose, having a 11,200 number average molecular weight, 1 weight percent ferric oxide and 0.25 weight percent magnesium stearate; and a semipermeable wall comprising 97 weight percent cellulose acetate having an acetyl content of 39.8% and 3 weight percent polyethylene glycol having a molecular weight of 4000. The device comprises a 20 mil (0.52 mm) exit orifice.

EXAMPLE 8-9

An osmotic dosage form is prepared by following the above described manufacturers. In this example, the first contraceptive composition in the compartment of the osmotic dosage form comprises 0.035 mg of 17α-ethinyl estradiol, 0.50 mg of D-17β-acetoxy-13β-ethyl-17α-ethinyl -gon-4-en-3-one oxime, polyethylene oxide having a 100,000 molecular weight, hydroxypropylmethylcellulose having a 11,200 molecular weight and the lubricant magnesium stearate.

An osmotic dosage form is prepared wherein the first composition is 1.5 mg of 13β-ethyl-17α-ethinyl-17β-hydroxygon-4-en-3-one, 0.05 mg of ethinyl estradiol, polyethylene oxide having a 135,000 molecular weight, hydroxypropylmethylcellulose having a 22,500 molecular weight, and the lubricant stearic acid.

EXAMPLE 10

Figure 11:
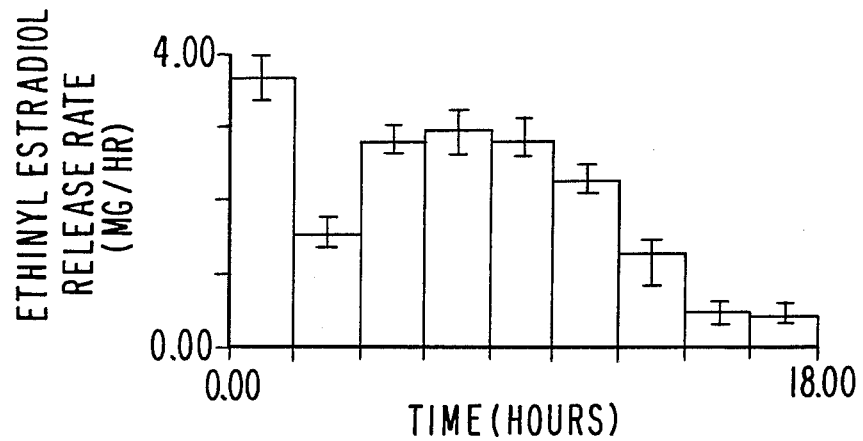
Figure 12:
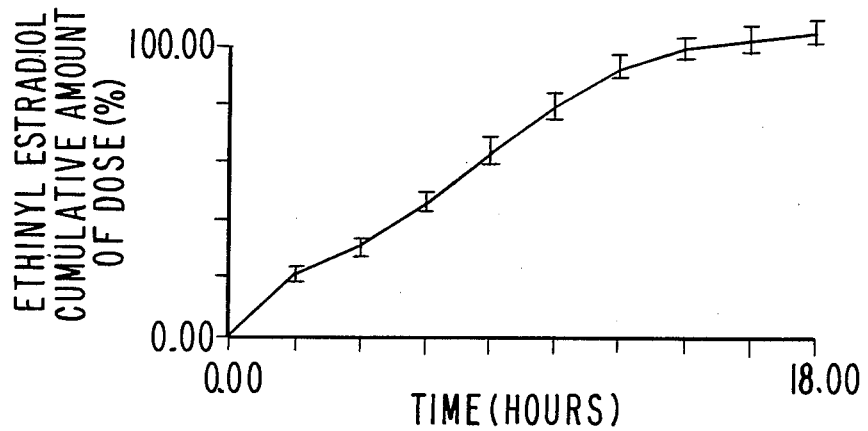

A contraceptive dosage form for oral administration to a patient desiring contraception is prepared by following the above procedures. In this example the dosage form provided is as follows: a first contraceptive composition weighing 30 mg and comprising 0.13 wt% ethinyl estradiol, 1.47 wt% norethindrone, 92.9 wt% polyethylene oxide possessing a 100,000 molecular weight, 5 wt% hydroxypropylmethylcellulose possessing a 11,200 molecular weight, and 0.5 mg of magnesium stearate; a second push composition for applying a force against the first composition for pushing it from the dosage form, wherein the second composition weighs 30 mg and comprises 74 wt% of a polyethylene glycol possessing a 7,500,000 molecular weight, 20 wt% of sodium chloride, 5 wt% of hydroxypropylmethylcellulose possessing a 11,200 molecular weight, 0.5 wt% of FD & C blue like #1 dye, and 0.5 wt% of magnesium stearate. The dosage form comprises a semipermeable wall weighing 7.00 mg, which wall comprises 95 wt% of a cellulose acetate comprising a 43.5% acetyl content and 5 wt% of polyethylene glycol possessing a 3350 molecular weight. An instant steroid release overcoat is in contact with the exterior surface of the semipermeable wall, which instant overcoat comprises 0.70 wt% ethinyl estradiol, 90 wt% hydroxypropylmethylcellulose possessing a 11,200 molecular weight and 9.30 wt% of polyethylene glycol possessing a 3350 molecular weight. In an optional embodiment a second steroid-free overcoat on the outermost surface of the dosage form weighs 2.00 mg and comprises 90 wt% hydroxypropylmethylcellulose possessing a 11,200 molecular weight and 10 wt% of polyethylene glycol possessing a 3350 molecular weight. The dosage form has an 0.52 mm exit passageway. The ethinyl estradiol release rate is depicted in FIG. 11 and the cumulative amount of ethinyl estradiol released over 18 hours is depicted in FIG. 12.

METHOD OF USING THE INVENTION

An embodiment of the invention pertains to a method for delivering the beneficial contraceptive steroids orally at a rate controlled dose to a female recipient in need of contraception. The method comprises the steps of: (A) admitting into the female an osmotic dosage form comprising: (1) a wall surrounding a compartment, the wall comprising at least in part a semipermeable polymer composition permeable to the passage of fluid and substantially impermeable to the passage of contraceptive steroid; (2) a composition comprising a contraceptive estrogen steroid and a contraceptive progestogen steroid in the compartment in an amount for performing a contraceptive program; (3) a layer in the compartment for imbibing and absorbing fluid for pushing the composition from the osmotic dosage form; and (4) at least one passageway in the wall for releasing the composition from the dosage from; (B) imbibing fluid through the semipermeable part of the wall at a rate determined by the permeability of the semipermeable wall and the osmotic pressure gradient across the semipermeable wall thereby causing the osmotic layer to expand and swell; and (C) delivering the contraceptive steroids from the dosage from through the exit passageway to the recipient of a contraceptive program selected from the group consisting of: (a) administering the osmotic dosage from for 4 to 6 days wherein the daily dose delivered corresponds to an estrogenic activity of 0.020 to 0.050 mg of 17α-ethinyl estradiol and a progestogenic activity of 0.050 to 0.125 mg of d,l-norgestrel, then for 4 to 6 days at an estrogenic delivered dose of from 0.020 to 0.100 mg and a progestogenic delivered dose of from 0.050 mg to 0.200 mg, followed by the next 9 to 11 days of from 0.020 to 0.100 mg of estrogenic activity and progestogenic activity of 0.050 to 0.250 mg of d,l-norgestrel; (b) the osmotic dosage from is administered for 21 successive days comprising for the first 5 to 8 days a delivered progestogen equivalent to about 0.065 to 0.75 mg of norethindrone in combination with an estrogen equivalent of from 0.020 to 0.050 mg of 17α-ethinyl estradiol, then for 7 to 11 days administering an osmotic dosage form that delivers a progestogen dose equivalent to 0.250 to 1.00 mg of norethindrone accompanied with an estrogen dose equivalent to 0.020 to 0.50 mg of ethinyl estradiol, which is followed by administering an osmotic dosage form for 3 to 7 days that delivers a daily progestogen equivalent of about 0.35 to 2.0 mg of norethindrone together with an estrogen equivalent of about 0.02 to 0.05 mg of ethinyl estradiol; (c) administering an osmotic dosage form for 21 successive days that delivers for the first 5 to 8 days a combination of an estrogen and a progestogen wherein the dose of progestogen is equivalent to 0.065 to 0.75 mg of norethindrone and the estrogen is the equivalent to about 0.02 to 0.05 mg of ethinyl estradiol; followed by administering an osmotic dosage form for 7 to 11 days that delivers a daily dose of progestogen equivalent to 0.25 to 1.0 mg of norethindrone along with an estrogen equivalent of 0.020 to 0.50 mg of ethinyl estradiol, and then administering the osmotic dosage form for 3 to 7 days which dosage form delivers a daily dosage of a progestogen equivalent to about 0.35 to 2.0 mg of norethindrone in combination with an estrogen equivalent to about 0.02 to 0.05 mg of ethinyl estradiol; (d) administering an osmotic dosage form for 5 to 8 days that delivers each day an estrogen in an amount sufficient to result in an equivalent effect of 0.02 to 0.40 mg of ethinyl estradiol and a progestogen to produce a contraceptive effect equivalent to 0.30 to 0.80 mg of norethindrone, followed by administering the osmotic dosage form for 7 to 11 days to produce an estrogenic contraceptive effect of 0.02 to 0.80 mg of ethinyl estradiol and a progestogen contraceptive effect of 0.30 to 1.60 mg of norethindrone, and then administering for 3 to 7 days the osmotic dosage form wherein the dosage delivered per day is an estrogen equivalent to 0.02 to 0.40 mg of ethinyl estradiol and a progestogen equivalent of 0.30 to 0.80 mg of norethindrone; (e) administering for 7 days an osmotic device that dispenses 0.050 mg of estradiol valerate and 0.125 mg of levonorgestrel, followed by 7 days of 0.050 mg of estradiol valerate and 0.75 mg of levonorgestrel, and then for 7 days an osmotic dosage form that delivers 0.050 mg of estradiol valerate and 0.50 mg of levonorgestrel, to produce, according to at least one of the contraceptive programs, the desired contraceptive effect.

While, the invention has been described and pointed out in details, as applied to preferred embodiments, those skilled in the art will appreciate that various modifications, changes and omissions in the delivery system and the delivery program described herein can be made without departing from the spirit of the invention.

We claim:

1. An osmotic device for delivering contraceptive steroids, the osmotic device comprising:
   (a) a wall comprising at least in part a composition permeable to the passage of fluid, which wall surrounds;
   (b) a compartment;
   (c) at least one exit passageway that connects the exterior of the device with the compartment;
   (d) a first composition in the compartment, said composition comprising a contraceptively effective amount of an estrogenic steroid and a contraceptively effective amount of a progestogenic steroid; and,
   (e) a second composition in the compartment, said second composition comprising an osmopolymer which composition, when the device is in operation in the presence of fluid that enters the device, increases in dimensions and displaces the first composition through the passageway from the device.

2. The osmotic device for delivering the contraceptive steroids according to claim 1, wherein the contraceptive steroids are delivered as an estrogenic and progestogenic contraceptive pair simultaneously from the device.

3. The osmotic device for delivering the contraceptive steroids according to claim 1, wherein the estrogenic and the progestogenic steroids are delivered in a ratio that corresponds to their initial ratio in the device for fertility control.

4. The osmotic device for delivering the contraceptive steroids according to claim 1, wherein the estrogenic and the progestogenic steroids are delivered in an amount per unit time that corresponds to their concentration in the device.

5. The osmotic device for delivering the contraceptive steroids according to claim 1, wherein the estrogenic steroid is a member selected from the group consisting of estradiol, estradiol valerate, estradiol benzoate, estradiol cypionate, estradiol propionate, estradiol dipropionate, estradiol acetate, ethinyl estradiol, ethinyl estradiol esters, ethinyl estradiol acetate, ethinyl estradiol benzoate, ethinyl estradiol ethers, estrone, estrone acetate, estrone sulfate, estriol, estriol succinate and estriol triacetate.

6. The osmotic device for delivering the contraceptive steroids according to claim 1, wherein the progestogenic steroid is a member selected from the group consisting of progesterone, d,l-norgestrel, norethindrone, levonorgestrel, norgestimate, 3-ketodesogestrel, desogestrel, gestodene, norethisterone, norethisterone acetate, norethynodrel, norethindrone acetate, hydroxyprogesterone, hydroxyprogesterone esters, 19-norhydroxyprogesterone, 19-nor-17-hydroxyprogesterone esters, 17α-ethinyl testosterone, 17α-ethinyl-19-nortestosterone, D-17β-acetoxy-13β-ethyl-17α-ethinyl-gon-4-en-3-one oxime, d-13β-ethyl-17α-ethinyl-17β-hydroxygon-4-en-3-one, 13β-ethyl-17β-hydroxygon-4-en-3-one, 13β, 17β-diethyl-17β-hydroxygon-4-en-3-one, ethynodiol diacetate, medroxyprogesterone, chlormadione acetate, medroxyprogesterone acetate, megestrol acetate, dimethistrone, and 17α-ethinyl-17β-acetoxy-19-norandrost-4-en-3-one oxime.

7. The osmotic device for delivering the contraceptive steroids according to claim 5, wherein the device comprises 0.002 mg to 0.500 mg of the estrogenically active steroid.

8. The osmotic device for delivering the contraceptive steroids according to claim 6, wherein the device comprises 0.005 mg to 250 mg of the progestogenically active steroid.

9. The osmotic device for delivering the contraceptive steroids according to claim 1, wherein the estrogenic and the progestogenic steroids are a pair selected from the group consisting of a contraceptive pair of ethinyl estradiol and norethindrone, ethinyl estradiol and d,l-norgestrel, ethinyl estradiol and norethisterone, ethinyl estradiol and 3-keto-desogestrel, ethinyl estradiol and desogestrel, ethinyl estradiol and gestodene, ethinyl estradiol and levonorgestrel, ethinyl estradiol and norgestimate, ethinyl estradiol and 17α-ethinyl-19-nortestosterone, ethinyl estradiol and 17α-ethinyl testosterone, ethinyl estradiol and D-17β-acetoxy-13β-ethyl-17α-ethinyl-gon-4-en-3-one oxime, ethinyl estradiol and d-13β-ethyl-17α-ethinyl-17β-hydroxygon-4-en-3-one, ethinyl estradiol and 13β-ethyl-17β-hydroxygon-4-en-3-one, ethinyl estradiol and 13β, 17α-diethyl-17β-hydroxygon-4-en-3-one, and ethinyl estradiol and 17α-ethinyl-17β-acetoxy-19-norandrost-4-en-3-one oxime.

10. The osmotic device for delivering the contraceptive steroids according to claim 1, wherein an estrogenic steroid is on the exterior surface of the wall.

11. The osmotic device for delivering the contraceptive steroids according to claim 1; wherein the wall carries on its outermost surface a progestogenic steroid.

* * * * *